(12) United States Patent
Abt

(10) Patent No.: US 11,517,474 B2
(45) Date of Patent: Dec. 6, 2022

(54) METHODS AND SYSTEMS FOR EYE ILLUMINATION

(71) Applicant: Novartis AG, Basel (CH)

(72) Inventor: Niels Alexander Abt, Winterthur (CH)

(73) Assignee: Alcon Inc., Fribourg (CH)

( * ) Notice: Subject to any disclaimer, the term of this patent is extended or adjusted under 35 U.S.C. 154(b) by 1034 days.

(21) Appl. No.: 16/213,361

(22) Filed: Dec. 7, 2018

(65) Prior Publication Data

US 2019/0183680 A1 Jun. 20, 2019

Related U.S. Application Data

(60) Provisional application No. 62/607,463, filed on Dec. 19, 2017.

(51) Int. Cl.

| A61F 9/007 | (2006.01) |
|---|---|
| A61B 90/00 | (2016.01) |
| A61B 90/30 | (2016.01) |
| G02B 21/36 | (2006.01) |
| G02B 21/00 | (2006.01) |
| G02B 21/06 | (2006.01) |
| A61B 3/113 | (2006.01) |
| A61F 9/008 | (2006.01) |

(52) U.S. Cl.
CPC .......... *A61F 9/00736* (2013.01); *A61B 3/113* (2013.01); *A61B 90/30* (2016.02); *A61B 90/361* (2016.02); *A61B 90/39* (2016.02); *G02B 21/0012* (2013.01); *G02B 21/06* (2013.01); *G02B 21/365* (2013.01); *G02B 21/368* (2013.01); *A61B 2090/395* (2016.02); *A61F 2009/00846* (2013.01); *A61F 2009/00872* (2013.01)

(58) Field of Classification Search
None
See application file for complete search history.

(56) References Cited

U.S. PATENT DOCUMENTS

| 7,784,946 | B2 | 8/2010 | LeBlanc |
|---|---|---|---|
| 8,371,695 | B2 | 2/2013 | Papac et al. |
| 8,398,236 | B2 | 3/2013 | Juhasz et al. |
| 9,119,565 | B2 | 9/2015 | Levis et al. |
| 9,597,009 | B2 | 3/2017 | Ren et al. |
| 9,645,379 | B2 | 5/2017 | Ren et al. |
| 2009/0124960 | A1 | 5/2009 | Mackool |
| 2009/0254070 | A1* | 10/2009 | Tripathi ............. A61B 3/13 606/4 |
| 2011/0157553 | A1* | 6/2011 | Moeller ............ A61B 3/113 351/209 |
| 2013/0296834 | A1 | 11/2013 | Wellhoefer et al. |

(Continued)

*Primary Examiner* — Kaitlin A Retallick

(57) ABSTRACT

Projection of visible, non-treatment light onto an eye to illuminate specific areas of the surgical field is disclosed herein. A surgical system may include a surgical console; a microscope communicatively coupled to the surgical console; a camera communicatively coupled to the surgical console; and a projector operable to project light onto an eye. The projector may be communicatively coupled to the surgical console. A method for light projection may include collecting information from an eye using a camera; determining the light projection based, at least in part, on the collected information; and projecting visible, non-treatment light onto the eye using a projector.

9 Claims, 9 Drawing Sheets

(56) References Cited

U.S. PATENT DOCUMENTS

2015/0305938 A1* 10/2015 Void .................. A61B 90/30
                                                            606/6
2016/0331584 A1   11/2016 Ren et al.
2017/0035287 A1    2/2017 Ren et al.
2017/0215726 A1*  8/2017 Spasovski ............ A61B 3/0008
2017/0280989 A1* 10/2017 Heeren .................. A61B 3/14
2017/0360605 A1* 12/2017 Oberkircher .......... A61F 9/0017

* cited by examiner

METHODS AND SYSTEMS FOR EYE ILLUMINATION

CROSS-REFERENCE TO RELATED APPLICATIONS

This application claims the benefit of U.S. Provisional Patent Application No. 62/607,463, filed Dec. 19, 2017, the entire contents of which are incorporated herein by reference.

TECHNICAL FIELD

The present disclosure relates to projecting light onto an eye to illuminate specific areas of the surgical field. The present disclosure also relates to projecting information onto an eye, for example, based on recognized features of the eye.

BACKGROUND

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinities.

In vitreoretinal surgery, the surgeon needs to visualize the posterior segment to properly address the eye condition. However, undesirable light, such as glare and/or glistening, from the surgical field may impact visibility of the posterior segment of the eye. Currently, vitreoretinal surgeons can work in a darkened operating room to decrease concerns with the undesired light. Alternatively, the operating room may not be darkened, but the vitreoretinal surgeon may then have difficulty visualizing the posterior segment due to the undesired light.

Access to the posterior segment in vitreoretinal surgery can be provided by one or more cannulas inserted into the eye. In the case of the darkened operating room, the surgical field (e.g., posterior segment, retina, etc.) can be illuminated with an endoilluminator disposed through a cannula. To introduce a new instrument through the cannula, the proximal end of the cannula (i.e., cannula hub) and the instrument will need to be visualized by the vitreoretinal surgeon. This often requires the vitreoretinal surgeon to zoom out the microscope and switch on the microscope light in order to visualize the proximal end of the cannula and the instrument and insert the instrument through the lumen formed in the cannula. Once the instrument is introduced into the eye through the cannula, the microscope light is switched off. While this technique provides light to introduce a new instrument through the cannula, the technique has drawbacks. For example, the time associated with readjustment of the microscope delays the vitreoretinal surgery.

SUMMARY

According to one aspect of the present disclosure, a surgical system for projecting illumination onto an eye is provided. The example surgical system may include a microscope; a cameral communicatively coupled to the surgical console, the camera operable to collect image data of an eye; a surgical console communicatively coupled to the camera, the surgical console operable to receive the image data; and a projector communicatively coupled to the surgical console and operable to project visible, non-treatment light onto an eye. The surgical console may include a processor and a memory. The memory may include code executable by the processor and the processor operable to process the image data in a manner defined by the code to identify one or more eye features. The projected visible, non-treatment light may be in the form of one or more discrete light projections directed to one or more particular locations of the eye based on the received image data.

Another aspect of the present disclosure is directed to a method of projecting light onto an eye. The method may include collecting image data of an eye using a camera; determining one or more discrete locations on the eye to be illuminated with projected light, the one or more discrete locations determined, at least in part, from the collected image data; projecting the visible, non-treatment light onto the one or more discrete locations of the eye using a projector.

Another aspect of the present disclosure is directed to a method of projecting light onto an eye. The method may include collecting image data of an eye using a camera; processing the received image data to determine one or more discrete locations on the eye to be illuminated with projected visible, non-treatment light; projecting light onto the one or more discrete locations of the eye to be illuminated, the one or more discrete locations being one or more cannulas disposed in the eye; and inserting a surgical instrument into at least one of the one or more cannulas while the light is being projected.

The different aspects may include one or more of the following features. The one or more eye features may include a feature of the eye or a feature disposed on the surface of the eye. The processor may be operable to determine the one or more particular locations on the eye based on the received image data. The image data of the eye may correspond to an image viewable through the microscope. The camera may be mounted to the microscope, and the projector may be mounted to the microscope. The one or more eye features may include a cannula inserted into the eye. The projected visible, non-treatment light may illuminate a discrete area of the eye surface that encompasses the cannula to the exclusion of the remainder of the eye surface. The projected light may include an incision marker, a toric axis, or a toric axis marker.

The different aspects may include one or more of the following features. Determining the one or more discrete locations on the eye to be illuminated with projected visible, non-treatment light may include processing the collected image using a processor to identify the one or more discrete locations. User input may be received, and the one or more discrete locations on the eye to be illuminated with projected visible, non-treatment light may also be determined based on the received user input. Projecting the visible, non-treatment light onto the one or more discrete locations of the eye using a projector may include projecting the visible, non-treatment light in a darkened operating room environment. The one or more discrete locations on the eye to be illuminated with projected light may include a feature of the eye or a feature disposed on the surface of the eye. A feature disposed on the surface of the eye may include and end of one or more cannulas disposed in the eye. A surgical instrument may be inserted into at least one of the one or more cannulas while the visible, non-treatment light is projected onto the one or more cannulas. Projecting visible, non-treatment light onto the one or more discrete locations of the eye may include projecting visible, non-treatment light in the form of a ring of light encircling a pupil of the eye. Projecting the visible, non-treatment light onto the one or more locations of the eye using a projector may include projecting the visible, non-treatment light onto the one or more discrete locations of the eye in the form of one or more incision markers. Projecting the visible, non-treatment light onto the one or more discrete locations of the eye using a projector may include projecting the visible, non-treatment light in the form of an incision spacing marker, an incision marker, a toric axis marker, or scleral flap marker. Projecting visible, non-treatment light onto the one or more discrete locations of the eye using a projector may include selectively illuminating the eye surrounding a pupil without illumination of the pupil. Projecting visible, non-treatment light onto the one or more discrete locations of the eye to be illuminated may include projecting a ring of the light onto the one or more cannulas. Projecting visible, non-treatment light onto the one or more discrete locations may include selectively illuminating each of the one or more cannulas to form a lighted zone at each of the one or more cannulas. Visible, non-treatment light may be projected onto the eye in the forms of one or more incision markers; one or more incisions may be formed in the eye according to the one or more incision markers; and one or more cannulas may be inserted into the eye through the one or more incisions.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
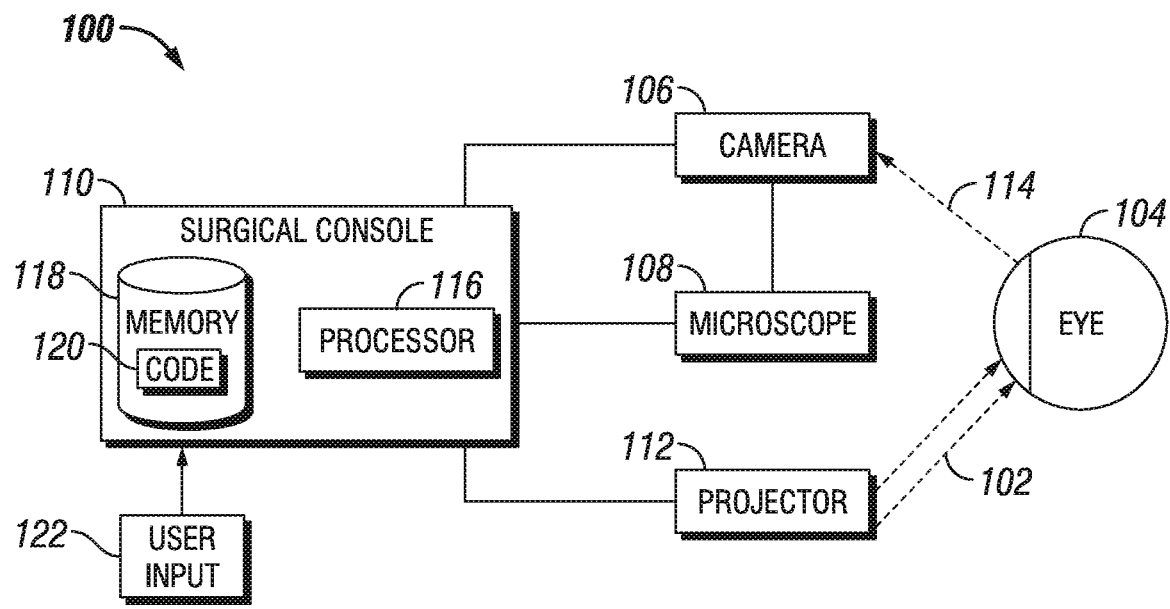
FIG. 1 is a block diagram of an example surgical system.

For the purposes of promoting an understanding of the principles disclosed herein, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles described herein are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The devices, instruments, methods, and other aspects described herein are made in the context of ophthalmology. However, the scope of the disclosure may be applicable to other medical arts. Consequently, the scope of the disclosure is intended to encompass other application within or outside of the medial arts.

The embodiments provided herein relate to ophthalmic surgery. More particularly, the embodiments generally relate to projecting visible, non-treatment light onto an eye to illuminate specific areas of a surgical field. The illumination projected onto a surface of the eye enables visualization of objects in specific areas within the surgical field, including, for example, an incision marker, selective illumination of an instrument inserted into the eye, an optical axis, or other symbols or information. For example, in a darkened operating room during vitreoretinal surgery, targeted illumination may be directed to a cannula located in an eye. The targeted illumination is focused so as to illuminate only the cannula or the cannula and a portion of the surgical field immediately adjacent to the cannula. That is, the targeted illumination is used to illuminate discrete portions of the eye associated with a specific area of the surgical, as opposed to a generalized illumination of the eye. The illumination may also include projection of light rays to provide information on the eye. This information may be used by a surgeon, for example, during the course of a surgical procedure. The information projected onto the eye may include, but is not limited to, an incision indicator (e.g., a cannula location indicator, a cataract incision indicator (Paracentesis), a glaucoma flap size and position indicator), and, in a case of toric IOL implantation, a toric axis indicator. The illumination may also include selective illumination such as glaucoma surgery illumination with the pupil shadowed or otherwise not illuminated. The illumination is non-treatment in that the illumination is not adapted to perform a surgical treatment to the eye but is merely provided for illumination purposes.

FIG. 1 illustrates an example surgical system 100 operable to project visible, targeted, and non-treatment light 102 onto an eye 104. As illustrated, the surgical system 100 includes a camera 106 that is operable to collect information on the eye 104 and a microscope 108 that is operable to visually inspect the eye 104. The surgical system 100 also includes a surgical console 110 that receives the information from the camera 106 and/or the microscope 108. By way of example, the surgical console 100 may process the information from the camera 106 to determine one or more locations on the eye 104 where light is to be projected for targeted illumination. The surgical system 100 also includes a projector 112 for projecting the targeted light 102 onto the eye 104.

The camera 106 collects information about the eye 104. For example, the camera 106 may collect one or more images of the eye 104, interchangeably referred to herein as image data. The image data may be real-time image data. The camera 106 provides the image data to the surgical console 106 for subsequent processing. The camera 106 may be any type of camera, including, but not limited to, CMOS and CCD monochromatic or color cameras, as well as color or monochromatic cameras with a broad wavelength in the visible range, as well as near infrared, or a very specific wavelength in visible-near-infrared range. Further, the camera 106 may be specifically tailored to detect a defined spectrum of electromagnetic wavelengths or one or more particular electromagnetic wavelengths, as desired. In some instances, the camera 106 may be configured to detect one or more electromagnetic wavelengths or a spectrum of electromagnetic wavelengths with the use of filters. The camera 106 communicates with the surgical console 110. For example, in some instances, the camera 106 may be in signal communication with the surgical console 110 via a wired or wireless connection. For example, the image data collected by the camera 106 may be sent to the surgical console 110 for further processing. In some embodiments, the camera 106 may be optimized for low light levels, such as in a vitreoretinal surgical environment where the operating room may be dark. In some embodiments, the eye 104 may be illuminated with light outside of the human visual range so as to avoid disturbing the surgeon. In such instances, the camera 106 may be of a type that is capable of detecting this light outside of the human visual range. The camera 106 is positioned and focused to receive reflected light 114 from the eye 104. In some embodiments, the camera 106 may use the reflected light 114 to image the eye 104 and provide information about the eye 114 to the surgical console 110.

The microscope 108 may be any microscope operable to visually inspect the eye 104. In some instances, the microscope 104 may be, although is not limited to, an ophthalmic surgical microscope or a stereo-microscope. A user, such as a surgeon or other medical professional, may operate the microscope 108 during surgery, for example, to visualize the eye 104 (or one or more specific regions thereof) in more detail. The microscope 108 also communicates with the surgical console 110. The microscope 108 may be in signal communication with the surgical console 110 via a wired or wireless connection. In some instances, the information collected by the microscope 108 is sent to the surgical console 110 for further processing. While not shown, the microscope 108 may include additional equipment, including, but not limited to, a light source.

The surgical console 110 includes one or more processors 116 and one or more memory devices 118. The processor 116 may be or include a microprocessor, a microcontroller, an embedded microcontroller, a programmable digital signal processor, or any other programmable device operable to receive information from the memory device 118 or other sources in communication with the processor 116 and perform one or more operations on the received information. The processor 116 may also be operable to output results based on the operations performed thereby. In some instances, the processor 116 may also be or include an application specific integrated circuit, a programmable gate array, programmable array logic, or any other device of combinations of devices operable to process electric signals.

In the illustrated example of FIG. 1, the memory device 118 is internal to the surgical console 110. However, in other implementations, the memory device 118 may be external to the surgical console 110. The memory device 118 may be a plurality of memory devices. In still other implementations, the memory device 118 may include one or more memory devices that are both internal and external of the surgical console 110. The memory device 118 may include any device operable to receive, store, or recall data, including, but not limited to, electronic, magnetic, or optical memory, whether volatile or non-volatile. The memory device 118 may include code 120 stored thereon. The code 120 may include instructions that may be executable by the processor 116. The code 120 may be created, for example, using any programming language, including but not limited to, C++ or any other programming language (including assembly languages, hardware description languages, and database programming languages). In some instances, the code 120 may be a program that, when loaded into the processor 116, causes the surgical console 110 to receive information from one or more of the camera 106 and microscope 108, determine one or more locations on the eye 104 needing illumination, and cause the projector 112 (described in more detail below) to project light onto the one or more determined locations.

In operation, the surgical console 110 receives information, e.g., image data, about the eye 104 from the camera 106. The information about the eye 104 received by the surgical console 110 from the camera 106 is processed by the processor 116. In some implementations, the camera 106 may include a separate processor, and the processor of the camera 106 may process the image data obtained by the camera 106. The processed image data may be transmitted to the surgical console 110. In some instances, the processor 116 may receive user input 122. The user input 122 may be information received from an input device, such as a keyboard, mouse, touch screen, or other input device by which a user inputs information. The processor 116 processes the information received from one or more of the camera 106, the user input 122, or one or more other sources to determine one or more locations on the eye 104 where light is to be projected, interchangeably referred to as desired light projection.

The desired light projection determined by the processor 116 is sent to the projector 112. The projector 112 projects light 102 onto the eye 104. In some instances, the desired light projection may be in the form of targeted illumination to illuminate one or more areas on the eye 104. In some instances, the desired light projection may be in the form of numerals, text, or other symbols projected onto a particular location of the surface of the eye. In still other implementations, desired light projection may include both targeted illumination as well as the projection of symbols, and the projector 112 may be operable to project both types of targeted illumination on the eye 104 at the same time.

According to other implementations, the camera 106, the microscope 108, and the projector 112 may be a stand-alone illumination system that operates independently of a surgical console, such as surgical console 110. In such implementations, one or more of the cameral 106, microscope 108, and projector 112 may include a processor and memory similar to the processor 116 and memory 118 described above. Code, similar to code 120, may be stored on the memory and executed by the processor to cause the illumination system to operate as described above. For example, the illumination system may operate in a similar manner to identify one or more areas of an eye to be illuminated with targeted light and cause the projector 112 to project targeted illumination onto the eye, as also described above. In some implementations, such an illumination system may be connected to a surgical console, such as, for example, surgical console 110, while, in other implementations, the illumination system may not be coupled to a surgical console.

The projector 112 includes any light source capable of generating the visible, targeted, and non-treatment light 102. For example, the light source may include, but is not limited to, light emitting diodes, organic light emitting diodes, and laser sources, which may either monochromatic, or in the red green blue color space, as well as other applicable type. The targeted light 102 from the projector may be projected onto discrete locations of the eye 104 to enable visualization of objects, such as a cannula (e.g., cannula illumination). Thus, the light 102 may be in the form of discrete areas of light projected onto particular, discrete areas of the eye surface in order to highlight the particular area or feature of or on the eye surface. That is, the light 102 is a targeted, and not a general, illumination of the eye surface. Projection of light 102 may be particularly applicable when done in a darkened operating room during vitreoretinal surgery. In some instances, the light 102 provided by the projector 112 may be or include an overlay into the surgical field. In still other instances, the light 102 provided by the projector 112 may be or include selective illumination of a particular region or regions of the eye, such as illumination with the pupil shadowed or otherwise not illuminated. This type of selective illumination may be particularly applicable to glaucoma surgery.

Figure 2:
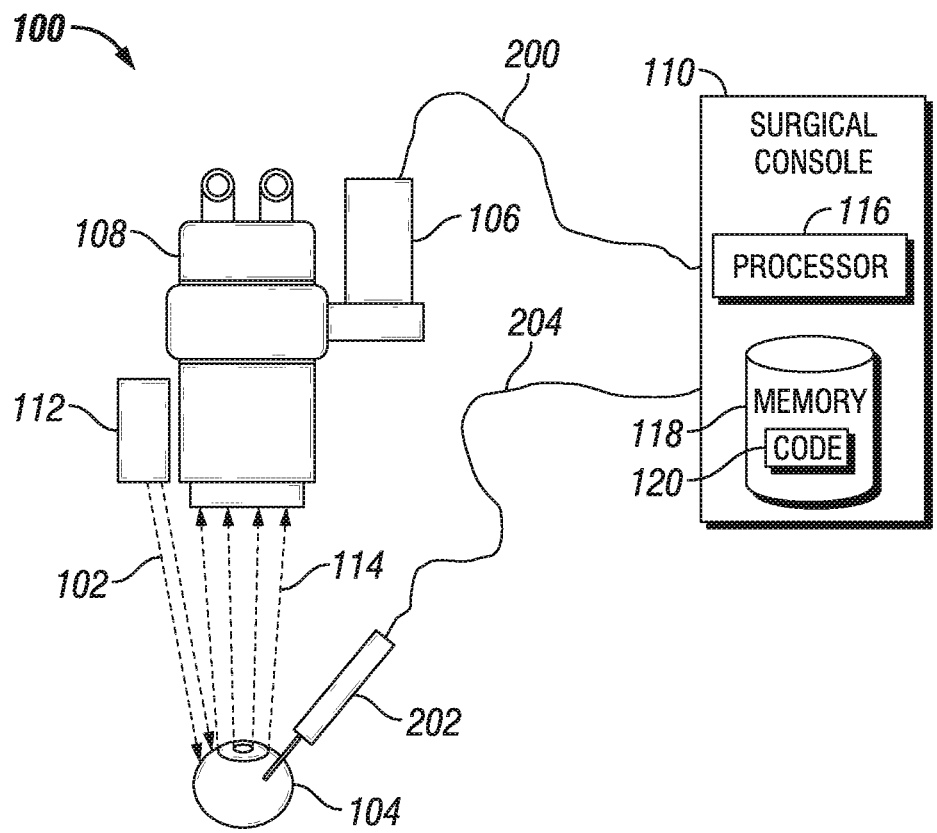
FIG. 2 is a schematic diagram of another surgical system.

FIG. 2 illustrates another example surgical system 100 operable to project the targeted light 102 onto the eye 104. In the illustrated embodiment, the surgical system 100 includes camera 106, a microscope 108, a surgical console 110, and a projector 112. The camera 106 collects information, in the form of image date, on the eye 104. As shown in FIG. 2, the camera 106 is mounted to the microscope 108. In other implementations, the camera 106 may be integrated into the microscope 108. For example, the camera 106 may be included in the optical path of the microscope 108, such as by a semi-transparent beam splitter. The camera 106 may be mounted to the microscope 108 in any desired manner. For example, the camera 106 may be mounted to the microscope 108 with the use of, fasteners, adhesives, or the like. In the illustrated embodiment, the camera 106 receives the reflected light 114 by way of the microscope 108. The information collected by the camera 106 is sent to the surgical console 110 through a communication line 200 that communicatively couples the camera 106 to the surgical console 110. As previously described, the surgical console 110 includes a processor 116 and a memory device 118 that includes code 120. The descriptions of the processor 116, memory device 118, and code 120 are applicable to the embodiment shown in FIG. 2 and are not repeated.

The desired light projection determined by the processor 116 is sent to the projector 112 for projecting the light 102 onto the eye 104. In some embodiments, the projector 112 may be mounted to the microscope 108. The projector 112 may be mounted to the microscope 108 in any desired manner. For example, the projector 112 may be attached or otherwise coupled to the microscope 108 with the use of fasteners, adhesives, or the like. While, in some implementations, the projector 112 may be mounted to the microscope 108, the scope of the disclosure is not so limited. Rather, in other implementations, the camera 106, the projector 112, or both may be provided separate from the microscope 108.

In the illustrated embodiment, the surgical system 100 may further include a surgical instrument 202. In some implementations, the surgical instrument 202 may be or include an instrument for use in a surgical procedure, including, but not limited to, an ophthalmic endoilluminator, a vitrectomy probe, forceps, scissors, backflush, soft tip cannula, pic, a scraper, or other surgical instrument. The surgical instrument 202 couples to the surgical console 110 via a connection line 202. In some implementations, the connection line 202 may provide power to the surgical instrument 202; data communication between the surgical console 110 and the surgical instrument 202; a passage for the communication for a fluid to or from the surgical instrument 202 (e.g., for irrigation, aspiration, or to power a fluidic motor of the surgical instrument 202); or a combination of any of these.

Figure 3:
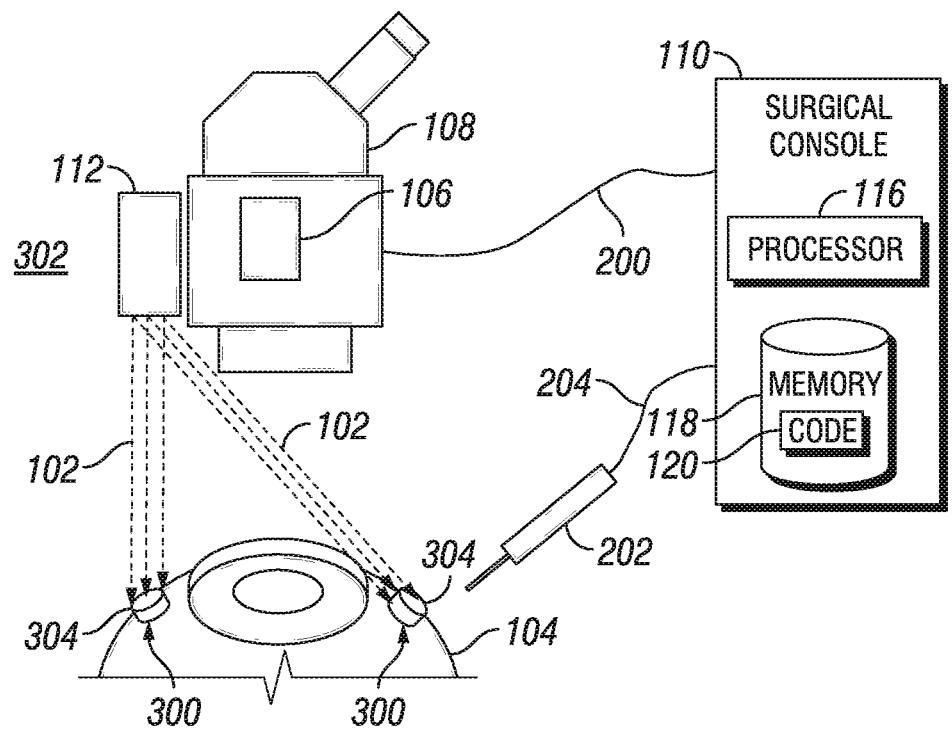
FIG. 3 is a schematic diagram showing an example cannula illumination system.

With reference now to FIG. 3, an example of using the surgical instrument 202 with projection of the targeted light 102 from the projector 112 will now be described. As illustrated, cannulas 300 are disposed in the eye 104. The cannulas 300 may include, but are not limited to, trocar cannulas and infusion cannulas. The cannulas 300 provide access into the eye 104. For example, the cannulas 300 may provide access into the eye 104 for the surgical instrument 202.

As previously described, operating room environment 302 may be darkened, for example, so that ambient light in the operating room environment 302 does not interfere with visualization through the microscope 108. With the operating room environment 302 in such a darkened state, a user may find inserting the surgical instrument 202 into one of the cannulas 300 to be difficult. As a result, the projector 112 may be configured to project the visible, targeted light 102 only onto proximal ends 304 of the cannulas 300. With this type of targeted illumination, the light 102 forms defined spots of light projected onto the eye surface that encompasses only the proximal ends 304 of the cannulas 300. In other instances, the spots of light formed by the light 102 projects onto the eye surface encompasses the proximal ends 304 of the cannulas 300 and a small portion of the eye surface immediately surrounding the proximal ends 304. A size of the visible spot of light created by the light 102 may be selected according, for example, to the preferences of a user. With the light 102 projected onto the proximal ends 304 of the cannulas 300 to form target areas of illumination, the cannulas 300 may be visualized, to the exclusion of other portions of the eye surface, even in the darkened environment 302 of an operating room so that a surgeon, for example, can locate the cannula 300 and insert the surgical instrument 202 thereinto.

Figure 4:
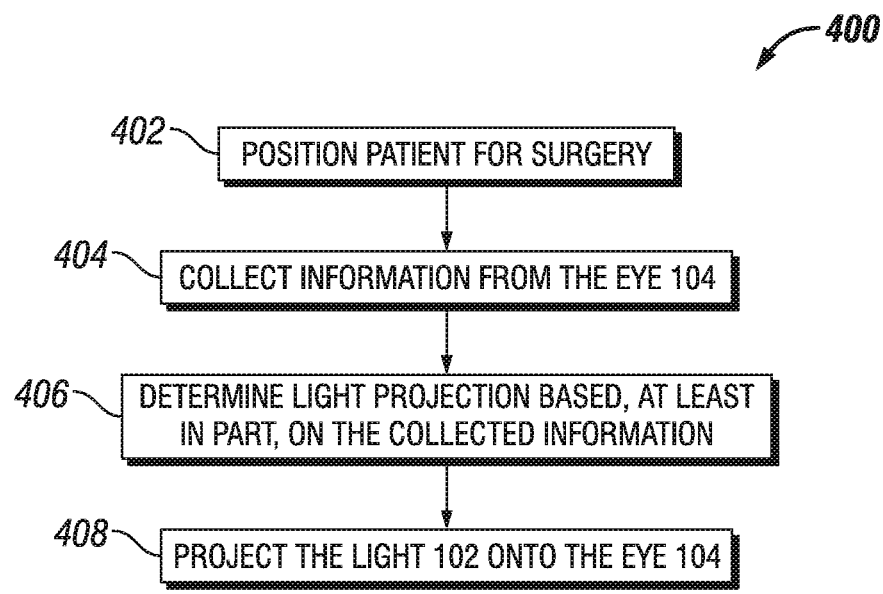
FIG. 4 is a flow chart illustrating an example method of light projection.

FIG. 4 is a flow chart illustrating an example method 400 of light projection. At 402, a patient is positioned for surgery. At 404, information from the eye 104 is collected. For example, a cameral, such as the camera 106 described above in the context of FIGS. 1-3, may be used to collect the information from the eye 104. The information received from the eye may be in the form of image data. The image data may be received by a camera and analyzed by a processor executing a program operable to detect one or more locations on the eye requiring illumination. The processed image data may indicate one or more locations on or in the eye where surgical devices are disposed. For example, the information received from the eye, once processed, may include location information of a cannula, such as cannula 300, disposed in the eye. At 406, one or more locations where light is to be projected is determined based, at least in part, on the information received from the eye. For example, a processor, such as the processor 116 described in the context of FIGS. 1-3, may operate to process the information received from the eye to determine one or more locations where light is to be projected onto the eye. At 408, light, such as the light 102 described above, is projected onto the eye 104. For example, a projector, such as the projector 112 described in the context of FIGS. 1-3, may operate to project the light onto the eye. The light projected by the projector may be both for illumination, projection of symbols or other information, or both.

Figure 5:
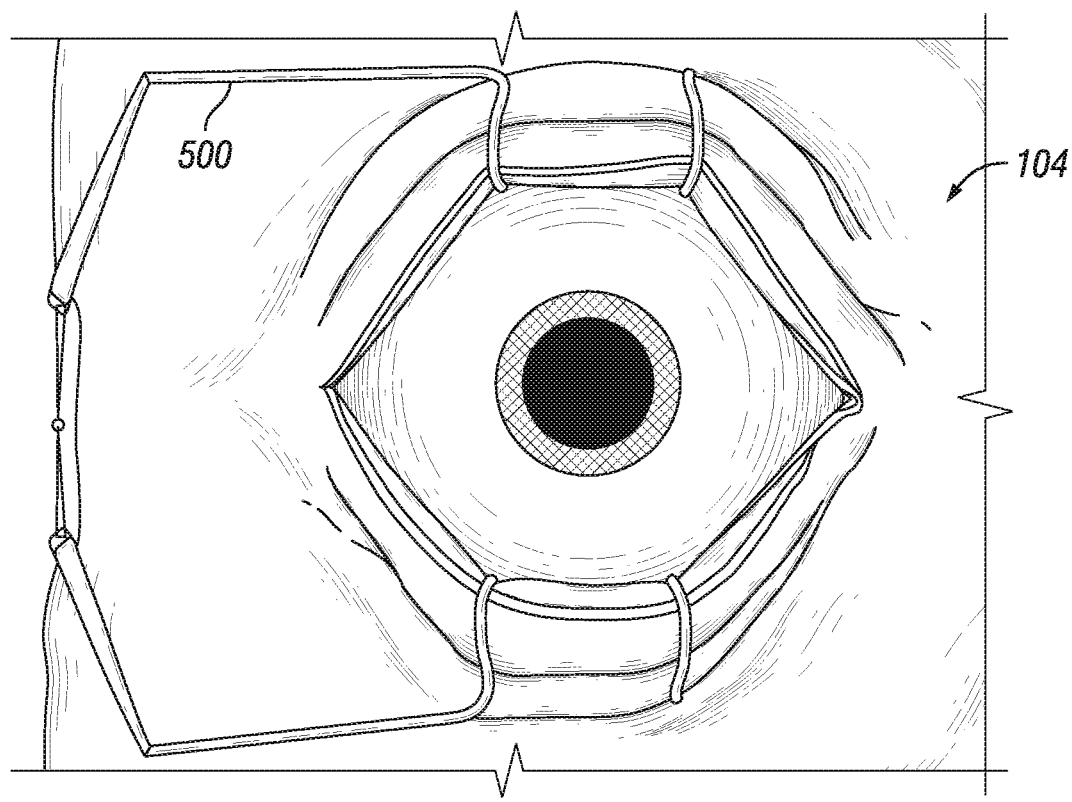
FIG. 5 illustrates an example of an eye free of illumination or projection.

FIG. 5 illustrates an example eye 104 on which no illumination or projection is being made. In FIG. 5, the eye 104 is positioned and prepared for a surgical procedure. As shown, a speculum 500 is positioned to hold the eye 104 in an open position during the surgical procedure.

Figure 6:
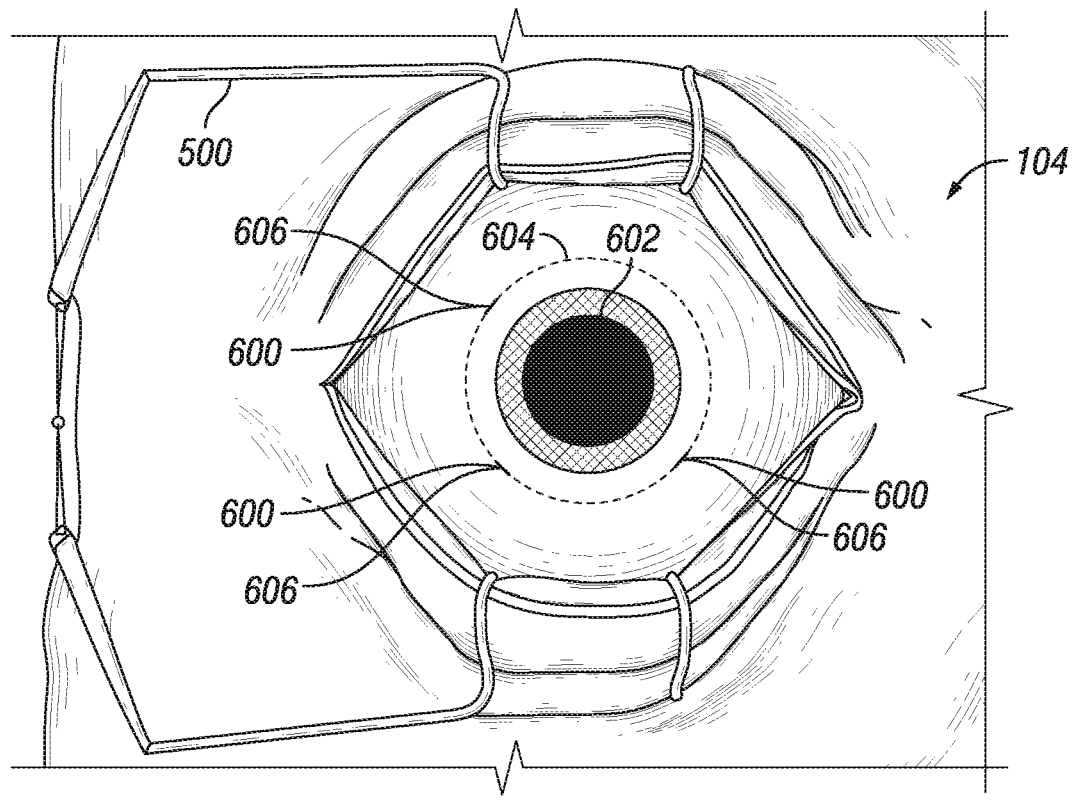
FIGS. 6-16 illustrate example different techniques for projection of light onto an eye.

FIG. 6 illustrates an example of light projection onto the eye 104. Particularly, FIG. 6 shows light projection in the form of incision markers 600. The incision markers 600 are discrete areas of illumination projected onto the eye surface in the form of arcs of visible light, as shown. In the illustrated example, the incision markers 600 are placed at locations along a circumference of an unfilled circle or narrow ring 604 projected onto the eye 104. In some instances, the entire circle 604 may be projected onto the eye 104. The incision markers 600 may also be projected onto the eye 104 in a manner, e.g., by a representation, that is distinguishable from the circle 604. In other implementations, the incision markers 600 may be omitted, and a surgeon, for example, may select a location where one or more incisions are to be made in the eye 104 at one or more locations along the circumference of the circle 604. In some instances, the circle 604 may not be projected onto the eye 104. Rather, in some instances, the incision markers 600 without the circle 604 may be projected onto the eye 104. Although numerous incision markers 600 are illustrated, in some implementations, a single incision marker 600 may be projected.

The incision markers 600 may be placed onto the eye 104 to indicate a desired spacing from pupil 602 of incisions 606 to be formed at the incision markers 600. By way of example, the incision markers 600 may indicate one or more locations on the eye (e.g., one or more locations on the sclera) at which the incisions may be made for insertion of the cannulas 300 as shown, for example, in FIG. 3. A surgeon may then proceed to make one or more incisions 606 along the incision markers 600.

Figure 7:
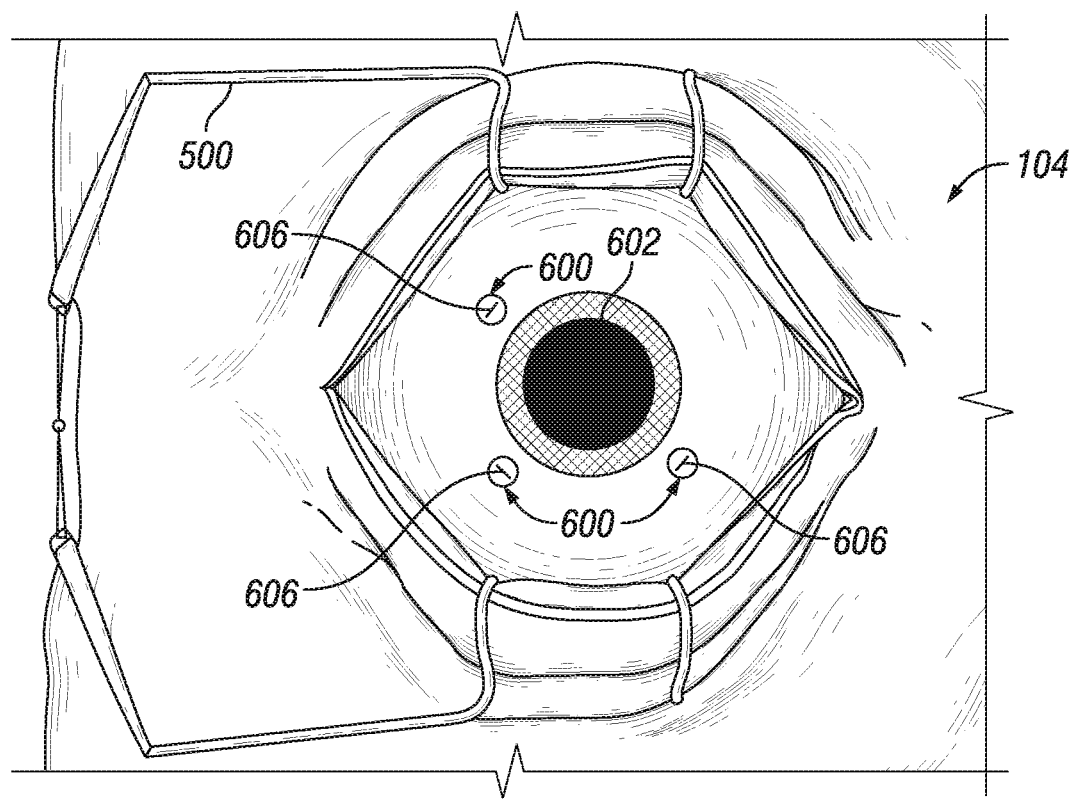

FIG. 7 illustrates another example embodiment of incision markers 600 projected onto the eye 104. FIG. 7 illustrates three projected incision markers 600, each of which is formed by a targeted light beam that illuminates a specified location of the eye surface to the exclusion of the other areas of the eye surface. The three projected incision markers 600 are located at a separate location on the eye 104. The incision markers 600 designate where placement of a cannula 300 (e.g., FIG. 3) is to be inserted into the eye 104 to provide access into an interior of the eye 104. A surgeon may then proceed to make one or more incisions 606 along the incision markers 600.

Figure 8:
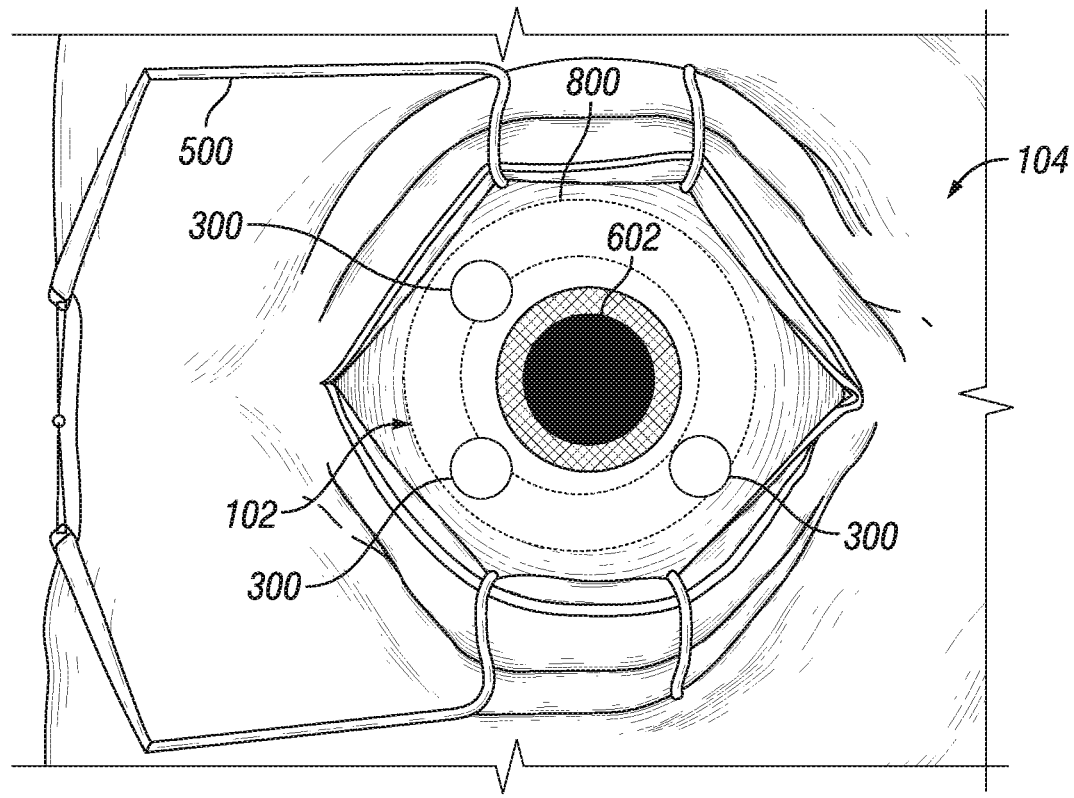
Figure 9:
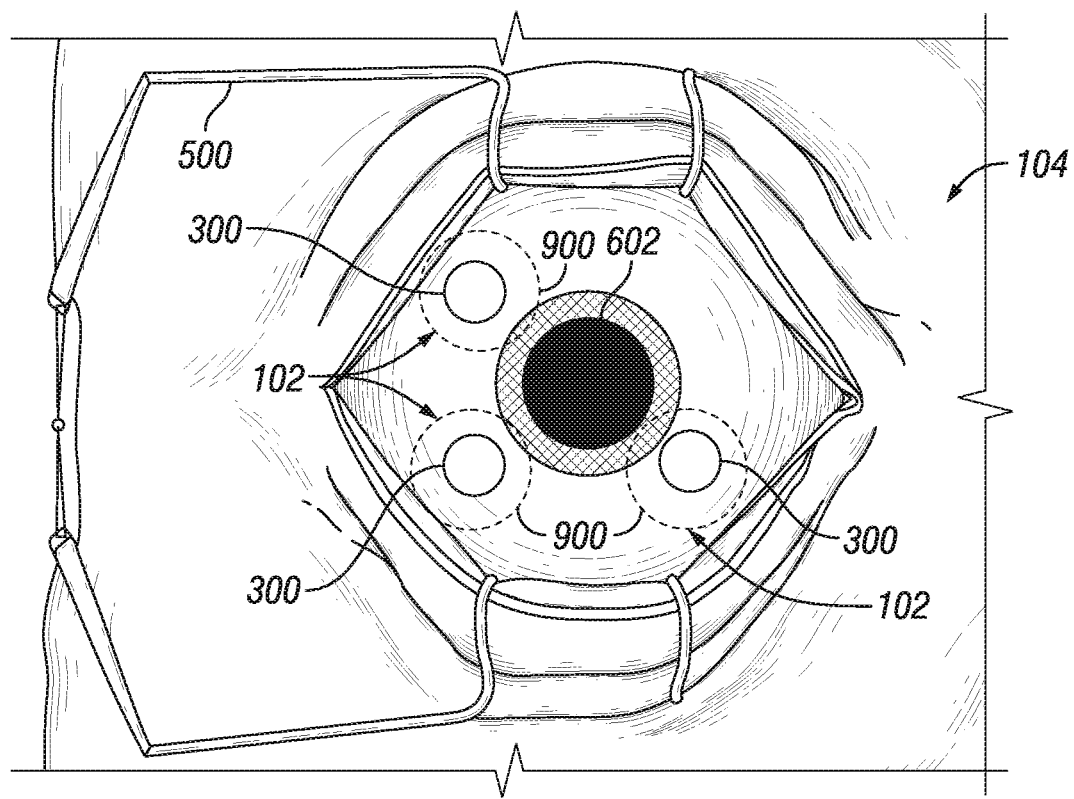

FIG. 8 illustrates yet another example of light projection onto the eye 104. As shown in FIG. 8, the light 102 is projected onto the eye 104 to illuminate one or more discrete areas on the surface of the eye 104 or one or more objects inserted into or otherwise present on the eye 104. In the illustrated example, a cannula 300 is shown inserted into the eye 104. As illustrated, the light 102 may be projected onto the eye 104 in the form of a ring 800 of the light 102 (indicated by the dotted circular lines) that encircles the pupil 602 and illuminates the cannulas 300. Thus, FIG. 8 illustrates an example in which a region of the eye 104 is illuminated by the light 102 contains multiple features, e.g., the multiple cannulas 300. FIG. 9 illustrates another example of light projection in which multiple, discrete instances of illumination are projected on to the eye 104. FIG. 9 shows a different region of illumination, each of the illumination regions being directed towards a single feature, e.g., a cannula 300. Instead of projecting the light in the form of the ring 800 encircling the pupil 102, as shown in FIG. 8, the light 102 is projected onto the eye 104 at each of the cannulas 300. That is, the light 102 may be projected onto the eye 104 in discrete light zones 900, each light zone 900 corresponding to a location where a cannula 300 is present. Thus, the light 102 may be projected onto the eye 104 to selectively illuminate each of the cannulas 300. As shown in FIG. 9, the light 102 forms a lighted zone 900 at each of the cannulas 300. The lighted zones 900 of visible light allows a user readily to identify the areas of the eye surface illuminated by the lighted zones 900.

Figure 10:
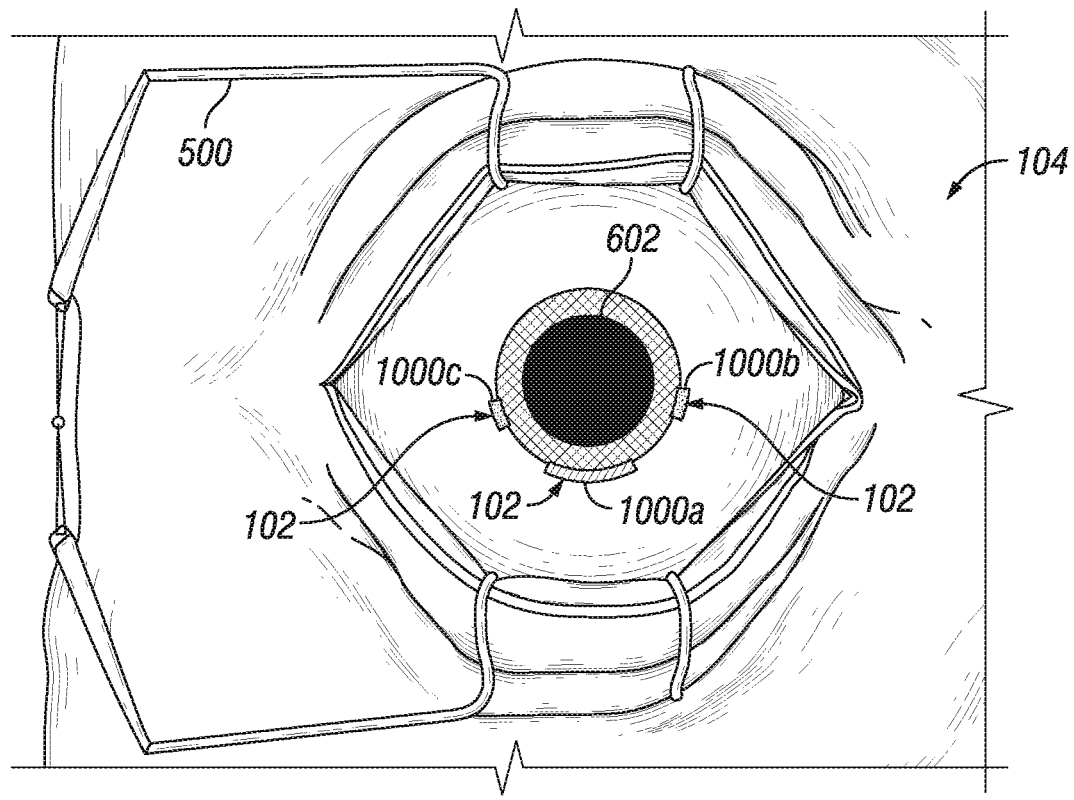
Figure 11:
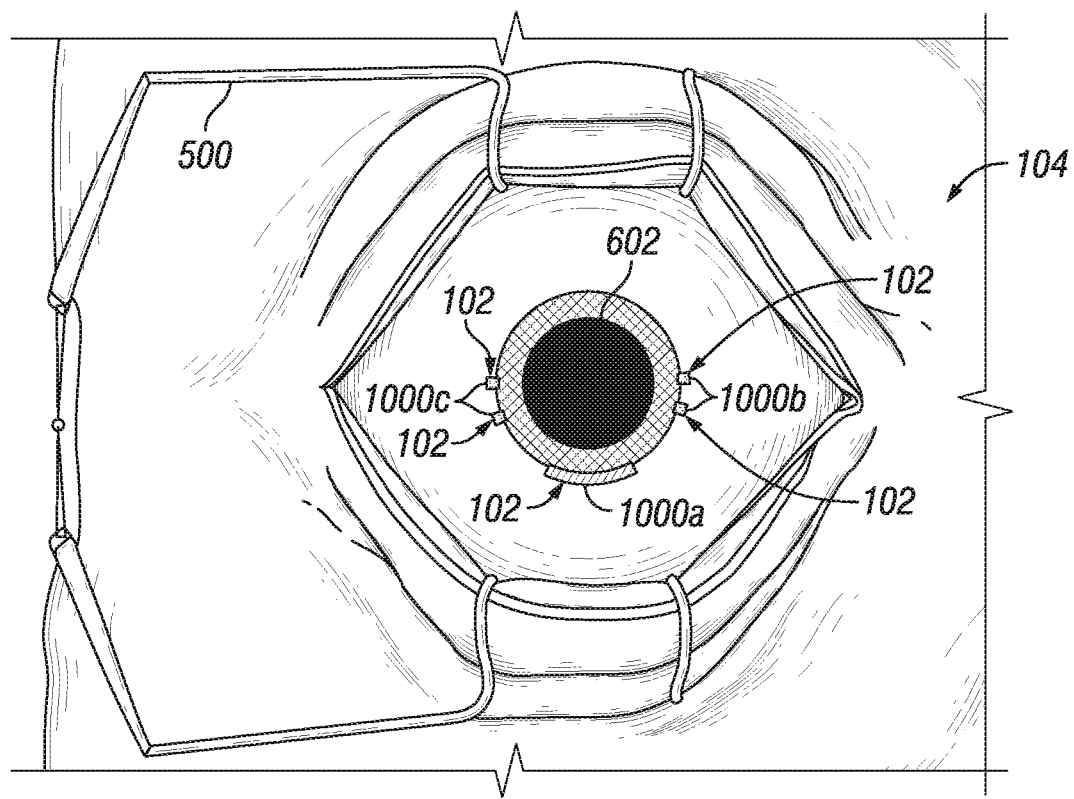

FIG. 10 illustrates another example of light projection onto the eye 104. As shown in FIG. 10, the targeted light 102 may be projected onto the eye 104 in a desired shape, e.g., in the form of an arc, for example, to indicate one or more incision locations 1000a, 1000b, and 1000c in cataract surgery. The projection of the one or more incision locations 1000a, 1000b, and 1000c may be sized different, for example, to reflect different sizes of the incisions to be made. The incision location 1000a may represent a main incision while incision locations 1000b and 1000c may represent paracentesis. As shown in FIG. 10, the light 102 of the light projection may designate different locations on the eye, and the light projections may have different sizes and shapes. In the particular illustrated example, a size of the light projection indicating incision location 1000a is larger than a size of the light projection indicating incision location 1000b or 1000c. Further, each of the light projections defining the incision locations 1000a, 1000b, and 1000c are in the form of an arc. However, the scope of the disclosure is not so limited. In other instances, the projected light may have or include other geometric shapes, symbols, or other indicators. FIG. 11 illustrates another example for projection of the light 102 onto the eye 104, for example, for use in cataract surgery. FIG. 11 illustrates the one or more incision locations 10000a, 1000b, and 1000c. The incision locations 1000b and 1000c may be in the form of small arc sections or boxes that indicate an extend of the incision to be made, while the incision location 1000a is marked with an arc shape similar to that shown in FIG. 10. As discussed above, the light 102 provides one or more visible indicators and is non-treatment in nature.

Figure 12:
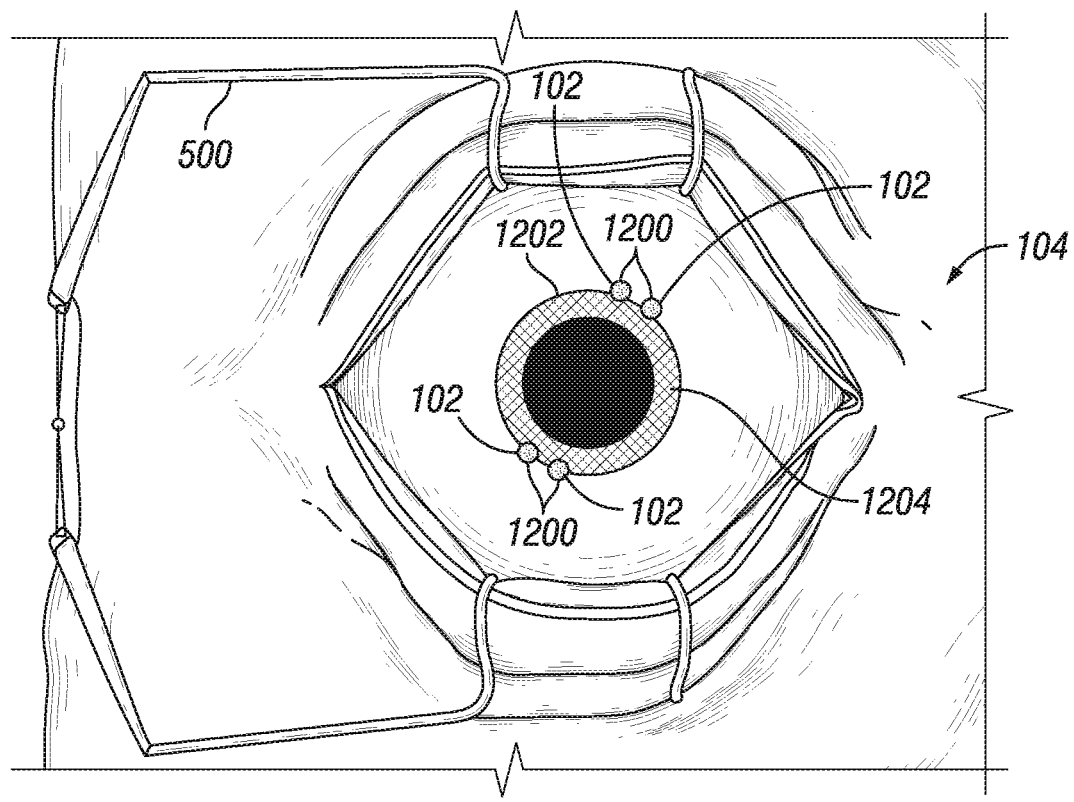

FIG. 12 illustrates another example of light projection onto the eye 104. In some procedures, such as cataract surgery, it may be desired to project a toric axis onto the eye 104, for example, in toric intraocular lens (IOL) implantation so that an implanted intraocular lens is oriented properly within the eye to provide the proper visual correction. FIG. 12 shows a light projection in which light 102 is projected onto the eye 104 in the form of toric axis markers 1200. The toric axis markers 1200 indicate a toric axis on the eye 104 to permit a user, such as a surgeon, to visualize a toric axis of the eye 104. In some embodiments, the toric axis markers 1200 may be placed at an edge 1202 of the cornea 1204, as shown on FIG. 12. The toric axis markers 1200 may provide a visual representation of the toric axis for the surgeon. In the illustrated example, the toric markers 1200 are in the form of filled-in circles. However, the scope of the disclosure is not so limited, and the toric axis markers 1200 may be any desired shape, character, symbol, or other indication.

Figure 13:
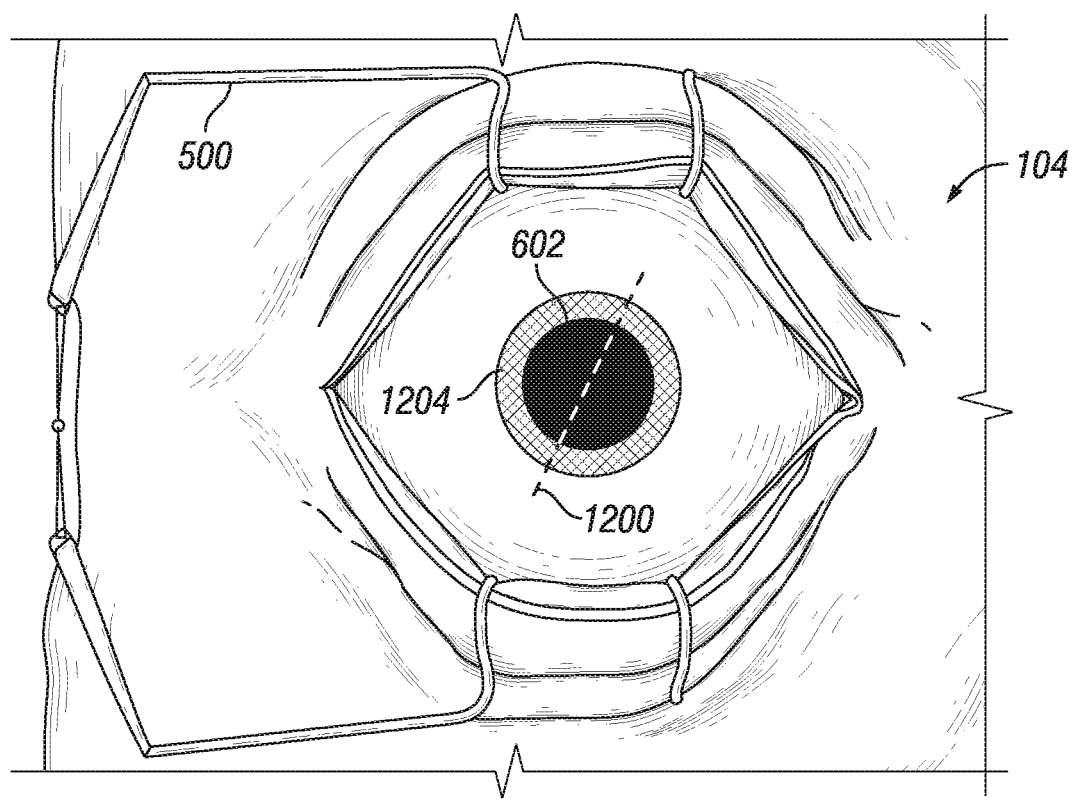
Figure 14:
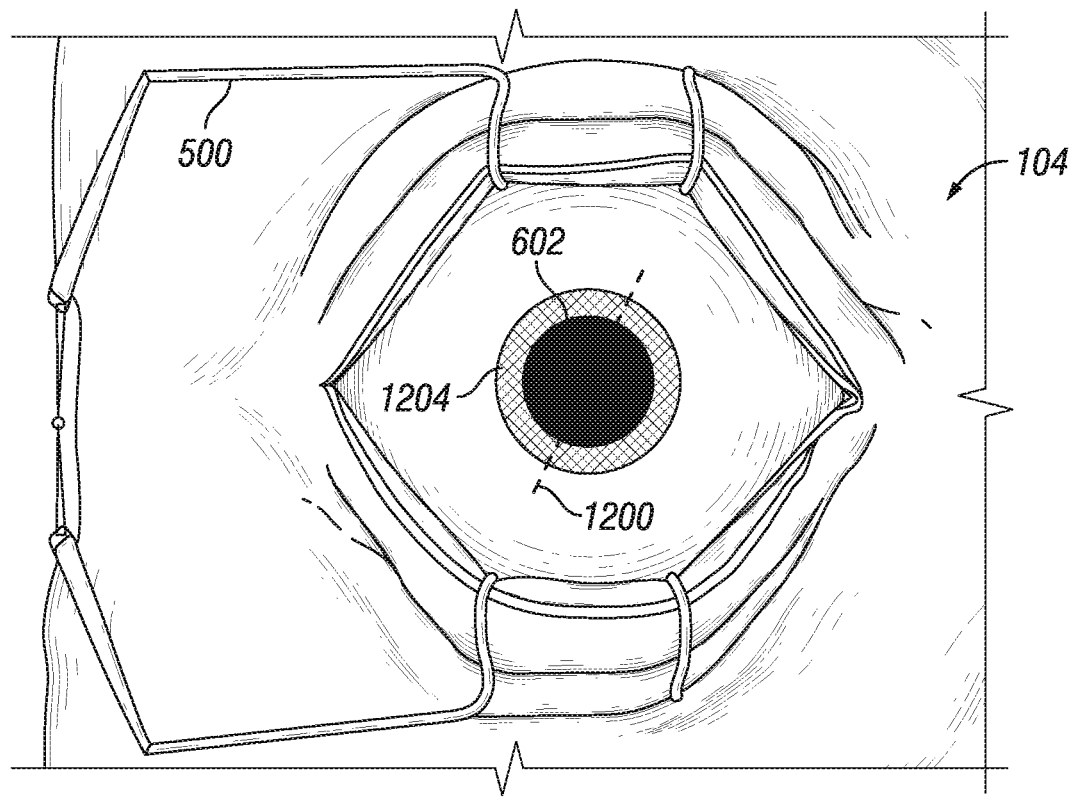

FIG. 13 illustrates another example embodiment for an overlay 600 that includes toric axis markers 1200. In the example of FIG. 13, the toric axis markers 1200 extend in a line across the cornea 1204 and pupil 602 to provide a visual representation of the toric axis to the surgeon. Although FIG. 13 shows the toric axis marker 1200 as being a dotted line, the toric axis maker 1200 may have other forms, such as, for example, a solid line. FIG. 14 illustrates another example embodiment light 102 being projected onto the eye 104 in the form of toric axis markers 1200. However, in the example of FIG. 14, the toric axis markers 1200 extend in a line through the cornea 1204, but the toric axis markers 1200 are not projected onto the pupil 602.

Figure 15:
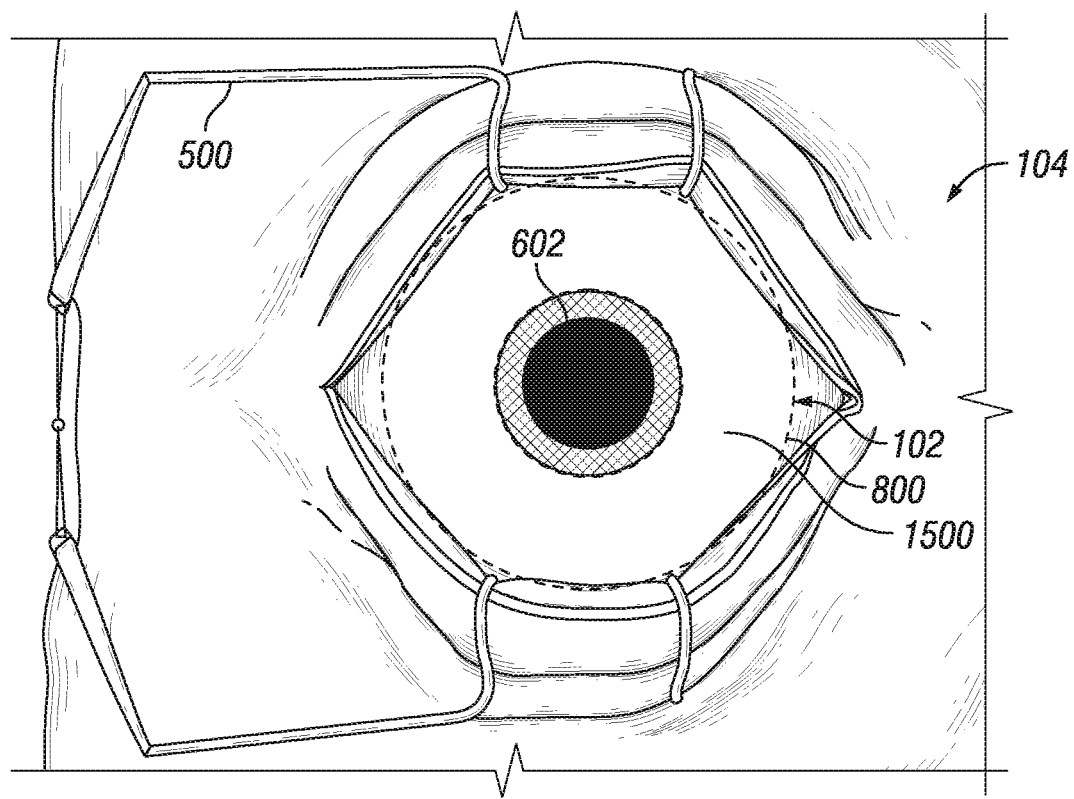

FIG. 15 illustrates another example of light projection onto the eye 104. In the embodiment of FIG. 15, the light 102 is projected onto the eye 104 in the form of a ring to provide selective illumination. In some procedures, such as glaucoma surgery, it may be desirable to illuminate some portions of the eye 104 while not illuminating others. As shown in FIG. 15, a portion of the sclera 1500 of the eye 104 is illuminated without illuminating the pupil 602. As illustrated, the light 102 may be projected in the form of a ring 800 of the light 102. The ring 800 of the light 102 may illuminate the eye 104 without illumination of the pupil 602.

Figure 16:
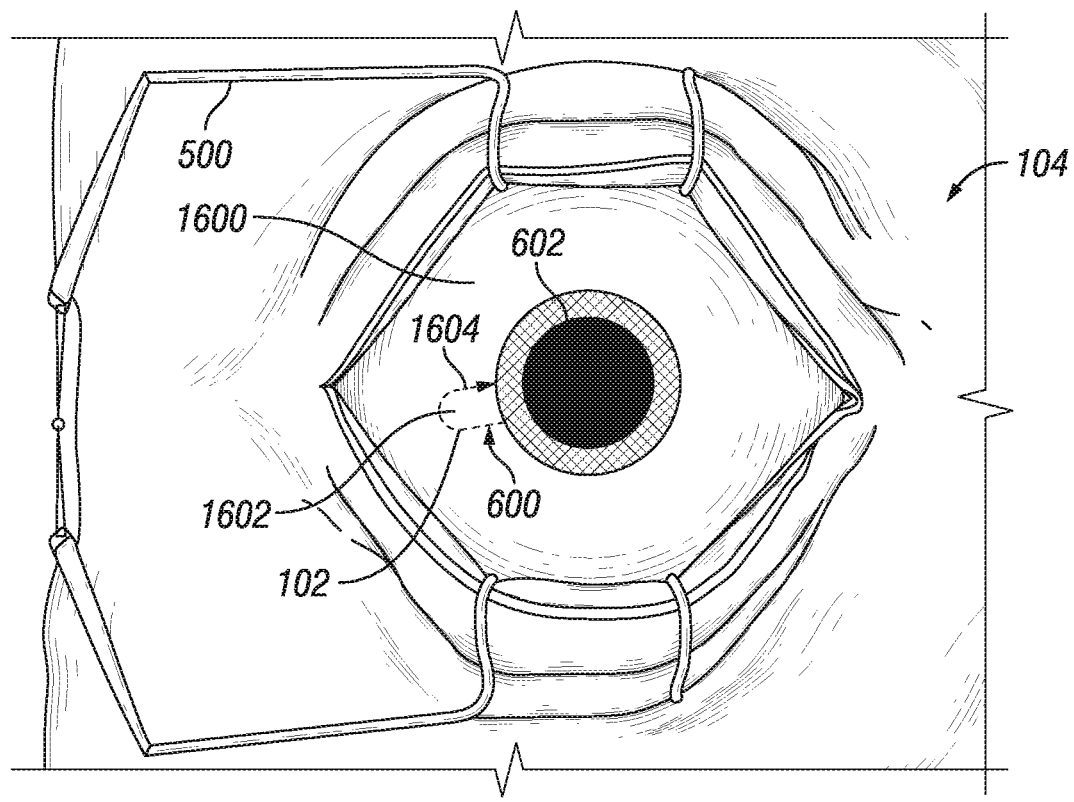

FIG. 16 illustrates another example of light projection onto the eye 104. In some procedures, such as a glaucoma surgical procedure, it may be desirable to make an incision in the sclera 1600 and form a scleral flap 1602. In the embodiment of FIG. 16, the light 102 is projected onto the eye 104 in the form of an incision marker 600. The incision marker 600 defines a scleral flap marker 1604. To make the scleral flap 1602, the surgeon may cut along the scleral flap markers 1604.

Figure 17:
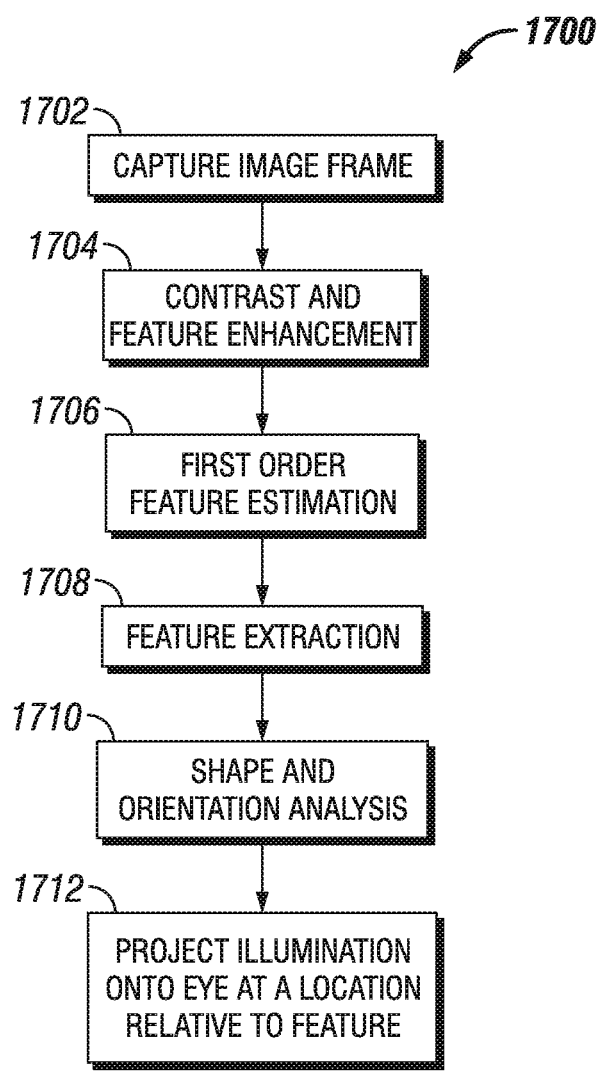
FIG. 17 is an example method for detecting one or more features on an eye for illumination.

FIG. 17 is a flowchart of an example method 1700 that may be used to detect one or more features on the eye for illumination. During a surgical procedure, ambient light within an operating room or light provided by a light source may provide imaging light to illuminate a surgical area, such as an eye of a patient. Reflected imaging light from the surgical area may be received by a camera, such as camera 106 described above. At 1702, the camera may capture images of the eye. In particular, the camera may capture frames of images to form a video. Each image frame may be forwarded to an image processor, which may be similar to a processor of a type described herein, e.g., processor 116, to be processed and analyzed. In some instances, the image processor may be separate from processor 116 included in the surgical console 110. In other instances, the processor 116 may operate as the image processor and may include code, whether forming part of code 120 or a separate code, to cause the processor 116 to process and analyze each image frame. Thus, in some instances, code running on the image processor, such as code 120, may provide the instructions to cause the image processor to process and analyze the received image frames.

At 1704, the image processor may perform contrast and feature enhancement processing on the image frame. For example, the image processor may receive the image frame in Red-Green-Blue (RGB) format. At 1704, the image processor may convert the RGB format image frame into a Hue-Saturation-Value (HSV) space; HSL (Hue, Saturation, Lightness) space; or Lab color space. HSV space is discussed in the examples described herein. However, HSV space is used merely as one possible red-green-blue (RGB) color model example, and it is understood that other color space models may also be used. At 1706, after the image frame has been enhanced to bring out the contrast and feature, the image processor may determine a first-order estimation mask of a feature of the eye or an item disposed on or extending into the eye. For example, the feature may be a pupil of an eye, an end of a cannula, or other feature. In some instances, the feature may be identified based on a predetermined color of the feature, a shape of the feature, or other predetermined characteristic. In the context of a predetermined color, the image processor 126 may apply criteria to the hue and saturation channels of the HSV image frame that may separate the feature from the background in order to bring out and estimate the image of the feature.

At 1708, the image processor may extract the image of the feature from the image frame. For example, the image processor may implement a blob detection process to detect a boundary of the feature in the image frame. A blob may be a region of the image frame where some properties, such as color and brightness, are approximately constant. The image processor may search for regions of approximately constant properties in the image frame to detect blobs. Thus, the image processor may find the boundary of a feature, such as, for example, a proximal end of a cannula inserted into an eye, and extract the feature from the image frame.

At 1710, the image processor may analyze the shape and orientation of the feature extracted from the image frame. Based on a predetermined pattern and color, the image processor may determine the orientation of the feature in the image frame.

At 1712, once the feature is identified, a processor, such as a processor of a type described herein, e.g., processor 116, directs a projector, such as projector 112, to project illumination towards the feature or onto the eye in a manner relative to the feature. For example, where the detected feature is a proximal end of a cannula, the processor may direct the projector to project illumination in the form of a lighted zone onto the proximal end of the cannula that closely approximates the shape of the proximal end of the cannula. In other instances, the processor may direct the projector to project illumination identifying incision markers, toric axis markers, or other types of markers or illumination zones onto an eye.

Although method 1700 illustrates an example process to detect one or more features on the eye for illumination, other methods to detect one or more features on the eye for illumination may include fewer, additional, and/or a different arrangement of operations. For example, the step of analyzing a shape and orientation of feature may be omitted.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A surgical system for projecting illumination onto an eye comprising:
   a microscope;
   a camera communicatively coupled to a surgical console, the camera operable to collect image data of an eye; and
   the surgical console communicatively coupled to the camera, the surgical console operable to receive the image data, the surgical console comprising:
      a processor; and
      a memory, the memory comprising code executable by the processor and the processor operable to process the image data in a manner defined by the code to identify one or more cannulas inserted into the eye;
   a projector communicatively coupled to the surgical console and operable to project visible, non-treatment light onto a surface of an eye, the projected light being in the form of one or more discrete light projections directed to one or more discrete area of the eye surface that encompasses the cannula to the exclusion of the remainder of the eye surface of the eye based on the received image data, wherein projecting visible, non-treatment light onto the one or more discrete locations comprises selectively illuminating each of the one or more cannulas to form a lighted zone at each of the one or more cannulas conforming to a shape of the cannula.

2. The surgical system of claim 1, wherein the processor is operable to determine the one or more particular locations on the eye based on the received image data.

3. The surgical system of claim 2, wherein the image data of the eye corresponds to an image viewable through the microscope.

4. The surgical system of claim 1, wherein the camera is mounted to the microscope, and wherein the projector is mounted to the microscope.

5. The surgical system of claim 1, wherein the projected light further comprises an incision marker, a toric axis, or a toric axis marker.

6. A method of projecting light onto an eye comprising:
   collecting image data of an eye using a camera;
   processing the received image data to determine one or more discrete locations on the eye to be illuminated with projected visible, non-treatment light;
   projecting visible, non-treatment light onto the one or more discrete locations of the eye to be illuminated, the one or more discrete locations being one or more cannulas disposed in the eye; and
   inserting a surgical instrument into at least one of the one or more cannulas while the visible, non-treatment light is being projected
   wherein projecting visible, non-treatment light onto the one or more discrete locations comprises selectively illuminating each of the one or more cannulas to form a lighted zone at each of the one or more cannulas, each of the lighted zones conforming to a shape of the cannula.

7. The method of claim 6, wherein projecting visible, non-treatment light onto the one or more discrete locations of the eye to be illuminated further comprises projecting visible, non-treatment light in an operating room environment.

8. The method of claim 6, wherein projecting visible, non-treatment light onto the one or more discrete locations of the eye to be illuminated further comprises projecting a ring of the light onto the one or more cannulas.

9. The method of claim 6, further comprising:
   projecting light onto the eye in the forms of one or more incision markers;
   forming one or more incisions in the eye according to the one or more incision markers; and
   inserting the one or more cannulas into the eye through the one or more incisions.

* * * * *